(12) United States Patent
Zhao et al.

(10) Patent No.: US 6,906,192 B2
(45) Date of Patent: Jun. 14, 2005

(54) PROCESSES FOR THE PREPARATION OF ACID DERIVATIVES USEFUL AS SERINE PROTEASE INHIBITORS

(75) Inventors: Rulin Zhao, Pennington, NJ (US); Bang-Chi Chen, Plainsboro, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 109 days.

(21) Appl. No.: 10/641,532

(22) Filed: Aug. 14, 2003

(65) Prior Publication Data

US 2004/0077865 A1 Apr. 22, 2004

Related U.S. Application Data

(63) Continuation-in-part of application No. 10/052,927, filed on Nov. 7, 2001, now Pat. No. 6,642,252.
(60) Provisional application No. 60/246,392, filed on Nov. 7, 2000.

(51) Int. Cl.$^7$ ............................................. C07D 217/12
(52) U.S. Cl. ...................................................... 546/143
(58) Field of Search ......................................... 546/143

(56) References Cited

U.S. PATENT DOCUMENTS

| | | | |
|---|---|---|---|
| 3,995,045 A | 11/1976 | Wade et al. | |
| 5,612,341 A | 3/1997 | Lee et al. | |
| 6,248,767 B1 | 6/2001 | Blok et al. | |
| 6,642,252 B2 | 11/2003 | Bisacchi et al. | |

FOREIGN PATENT DOCUMENTS

| EP | 0206567 | 12/1986 |
|---|---|---|
| GB | 2056968 | 3/1981 |
| JP | 3-7277 | 1/1991 |
| WO | WO 96/40111 | 12/1996 |
| WO | WO 97/31910 | 9/1997 |
| WO | WO98/47876 | 10/1998 |
| WO | WO98/57937 | 12/1998 |
| WO | WO 98/57937 | 12/1998 |
| WO | WO99/41231 | 8/1999 |
| WO | WO00/43374 | 7/2000 |
| WO | WO01/23374 A1 | 4/2001 |
| WO | WO01/44172 A1 | 6/2001 |
| WO | WO01/70678 | 9/2001 |
| WO | WO02/04423 A1 | 1/2002 |
| WO | WO02/24654 A1 | 3/2002 |
| WO | WO 02/34711 | 5/2002 |
| WO | WO 02/42273 | 5/2002 |

OTHER PUBLICATIONS

Kondo et al., Chem. Pharm. Cull. 42(1) pp. 62–66 (1994).

Takahasi et al., J. Chem. Soc. Perkin Trans. 1, (1993) pp. 1473–1479.

Xie, et al., J. Med. Chem., (1995) 38, pp. 3003–3008.

Pan et al., Journal of Medicinal Chemistry, (1970) vol. 13, No. 3 pp. 567–568.

Kesaru et al., Tetrahedron, vol. 48, No. 5 (1992) pp. 913–922.

Kohrt et al., Tetrahedron Letters, 41 (2000) pp. 6041–6044.

*Primary Examiner*—Zinna Northington Davis
(74) *Attorney, Agent, or Firm*—Anastasia P. Winslow; Jing G. Sun; Henry H. Gu

(57) ABSTRACT

This invention relates to novel processes for the preparation of amino isoquinolines, benzylamino isoquinolines, and acid derivatives useful as serine protease inhibtors.

6 Claims, No Drawings

PROCESSES FOR THE PREPARATION OF ACID DERIVATIVES USEFUL AS SERINE PROTEASE INHIBITORS

CROSS-REFERENCE TO RELATED APPLICATIONS

This application is a continuation-in-part of U.S. application Ser. No. 10/052,927 filed on Nov. 7, 2001 now U.S. Pat. No. 6,642,252, which claims the benefit of U.S. Provisional Application No. 60/246,392, filed Nov. 7, 2000; all of which are incorporated herein by reference.

FIELD OF THE INVENTION

The present invention relates to processes for the preparation of acid derivatives that are inhibitors of serine proteases such as Factor VIIa, Factor IXa, Factor Xa, Factor FXIa, tryptase, and urokinase. In particular, this invention relates to processes for prepartion of 1-aminoisoquinolines and related analouges, which are key intermediates for the synthesis of the acid derivatives. These acid derivatives are useful as anticoagulants in treating and preventing cardiovascular diseases, as anti-inflammatory agents, and as metastasis inhibitors in treating cancer.

BACKGROUND OF THE INVENTION

Early preparation of 1-aminoisoquinoline involved direct treatment of isoquinoline with an alkali amide such as sodium amide and potassium amide ($NaNH_2$, KNH2) via a Chichibabin type of reaction (for a review on Chichibabin reaction, see: McGill, C. K. and Rappa, A. *Advances in Heterocyclic Chemistry*, 1988, 44, 1–79). While this reaction is straight foreword for simple isoquinolines, it does not work well with those isoquinolines that have functional groups imcompatible with harsh condition using alkali amide (Rewinkel, J. B. M. et al. *Bioorganic & Medicinal Chemistry Letters*, 1999, 9, 685).

A more general approach to 1-aminoisoquinolines involves transformation of 1-hydroxyisoquinolines. In this approach the 1-hydroxy group was first converted to a better leaving group such as halides and phenoxides, followed by an aminolysis (Sanders, G. M., et al. *Recl. Trav. Chim. Pays-Bas*. 1974, 93, 198; Nuvole, A. and Pinna, G. A. *J. Heterocyclic Chem*. 1978, 15, 1513; Rewinkel, J. B. M. et al. *Bioorganic & Medicinal Chemistry Letters*, 1999, 9, 685; Rewinkel, J. B. M. et al. *Bioorganic & Medicinal Chemistry Letters*, 1999, 9, 2837; Zhang, P. et al. *Bioorganic & Medicinal Chemistry Letters*, 2002, 12, 1657; Choi-Sledeski, Y. M. et al. *Bioorganic & Medicinal Chemistry Letters*, 1999, 9, 2539). The 1-hydroxyisoquinolines starting materials used in this method were obtained by: (1) thermolysis of cinnamoyl azides (Choi-Sledeski, Y. M. et al. *Bioorganic & Medicinal Chemistry Letters,* 1999, 9, 2539); (2) oxidation of isoquinolines to isoquinoline N-oxides using peracids followed by rearrangement (Ochiai, K. *Pharm Bull*. 1957, 5, 606); or less commonly, transformation of 2-(β-carbamylvinyl)benzonitriles (Gabriel, *Chem. Ber*. 1916, 49, 1612). Direct transformation of isoquinoline N-oxides to 1-haloisoquinolines has also been reported (Rewinkel, J. B. M. et al. *Bioorganic & Medicinal Chemistry Letters*, 1999, 9, 685; Rewinkel, J. B. M. et al. *Bioorganic & Medicinal Chemistry Letters*, 1999, 9, 2837). This approach, however, suffered from long reaction sequences, use of hazardous reagents such as peracides and intermediates such as acyl azides.

Reaction of 2-methylbenzonitrile with 1-(t-butoxy)-N,N,N',N'-tetramethylmethanediamine to give 2-(2-dimethylaminovinyl)benzonitrile has been reported (Fisher, U. et al. *Helvetica Chimica Acta*, 1990, 73, 763).

SUMMARY OF THE INVENTION

The present invention is directed to a process for preparing an amino isoquinoline of the structure:

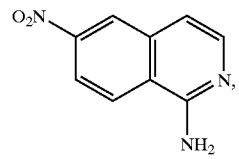

which comprises (a) reacting a cyanostyrene compound of the structure:

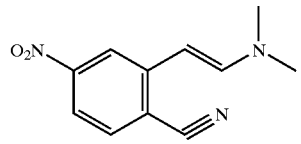

with lithium hexamethyl disilane to form the aminoisoquinoline; or (b) reacting a cyanostyrene of the structure:

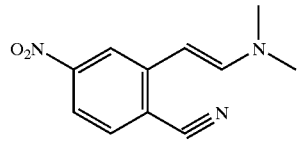

with 2,4-dimethoxylbenzylamine to form an isoquinoline of the structure

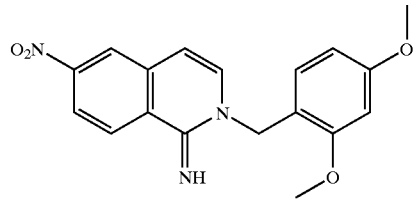

and reacting the isoquinoline with anisole to form the aminoisoquinoline.

This invention is also directed to a process for making a benzylamino isoquinoline compound of the structure:

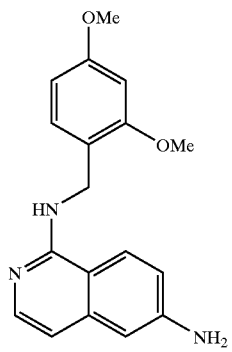

which comprises preparing an aminoisoquinoline

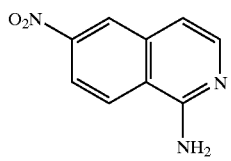

and employing the aminoisoquinoline to prepare the benzylaminoisoquinoline compound.

This invention is also directed to a process for preparing a compound of formula (I):

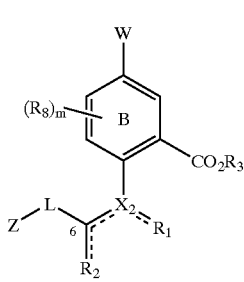

or a pharmaceutically-acceptable salt, hydrate or prodrug thereof, wherein:

W is selected from $C_{2-10}$alkyl, $C_{2-10}$alkenyl, substituted $C_{2-10}$alkyl, substituted $C_{2-10}$alkenyl, —C(=O)NR$_4$R$_5$, —OR$_6$, —CO$_2$R$_4$, —C(=O)R$_4$, —SR$_4$, —S(O)$_p$R$_4$, —NR$_4$R$_5$, —NR$_4$SO$_2$R$_5$, —NR$_{4a}$SO$_2$NR$_4$R$_5$, —NR$_4$CO$_2$R$_5$, —NR$_4$C(=O)R$_5$, —NR$_{4a}$C(=O)NR$_4$R$_5$, —SO$_2$NR$_4$R$_5$, heterocyclo, heteroaryl, aryl, and cycloalkyl;

ring B is phenyl or pyridyl;

X$_2$ is N, CH, or C, provided that X$_2$ is C when R$_1$ and R$_2$ join to form a fully unsaturated ring;

L is —(CR$_{18}$R$_{19}$)$_s$—Y—(CR$_{18a}$R$_{19a}$)$_t$;

Y is selected from —C(=O), —C(=O)NR$_{13}$—, —NR$_{13}$C(=O)—, —NR$_{13}$CR$_{14}$R$_{15}$—, —CR$_{14}$R$_{15}$—NR$_{13}$—, and —CR$_{13}$R$_{14}$—CR$_{15}$R$_{16}$—;

Z is a 5 to 7-membered monocyclic or 8 to 11-membered bicyclic aryl, heteroaryl, heterocyclo, or cycloalkyl, wherein each Z group is optionally substituted with up to two R$_{20}$ and/or up to one R$_{21}$, except Z is not phenyl substituted with phenyloxy when W is methoxy, s is 0 and Y is —CH$_2$—CH$_2$—;

R$_1$ and R$_2$ (i) are independently selected from hydrogen, alkyl, substituted alkyl, alkenyl, substituted alkenyl, heteroaryl, aryl, heterocyclo, and cycloalkyl; or (ii) are taken together to form an aryl, heteroaryl, cycloalkyl, or heterocyclo, provided that R$_1$ and R$_2$ do not together form pyrazole when W is methoxy and Z is biphenyl; and when R$_1$ and R$_2$ individually or together form a heteroaryl, aryl, heterocyclo, or cycloalkyl, said cyclic group is optionally substituted with up to three R$_{26}$;

R$_3$ is hydrogen, alkyl, substituted alkyl, heteroaryl, aryl, heterocyclo, cycloalkyl, or alkyl substituted with —OC(=O)R$_{24}$ or —OC(=O)OR$_{24}$, wherein R$_{24}$ is alkyl, substituted alkyl, or cycloalkyl, provided that R$_3$ is not phenyl when W is methoxy;

R$_4$, R$_{4a}$, R$_5$ and R$_6$ are (i) independently selected from hydrogen, alkyl, substituted alkyl, alkenyl, substituted alkenyl, alkynyl, substituted alkynyl, heteroalkyl, substituted heteroalkyl, aryl, heteroaryl, heterocyclo, and cycloalkyl; or alternatively, (ii) R$_4$ and R$_5$ may be taken together to form a five-to-seven membered heteroaryl or heterocyclo, except when W is —S(O)$_p$R$_4$, then R$_4$ is not hydrogen;

R$_8$ and R$_{26}$ (i) are at each occurrence independently selected from hydrogen, OR$_{30}$, NR$_{31}$R$_{32}$, NR$_{31}$SO$_2$R$_{32a}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl, or (ii) two of R$_8$ and/or two of R$_{26}$ may be taken together to form a fused benzo ring, a fused heteroaryl, a fused cycloalkyl, or a fused heterocyclo other than a five or six membered heterocyclo having as its heteroatoms two oxygen atoms, provided further that when two R$_{26}$ form a fused benzo ring, then Z is not phenyl substituted in the para position with cyano or a five-membered heterocycle or heteroaryl;

R$_{13}$, R$_{14}$, R$_{15}$, R$_{16}$, R$_{18}$, R$_{18a}$, R$_{19}$, and R$_{19a}$ are selected from hydrogen, lower alkyl, hydroxy, and lower alkyl substituted with hydroxy or halogen;

R$_{20}$ and R$_{21}$ are independently selected at each occurrence from hydrogen, halogen, alkyl, substituted alkyl, haloalkyl, haloalkoxy, cyano, nitro, —C(=O)NR$_{22}$R$_{23}$, —OR$_{22}$, —CO$_2$R$_{22}$, —C(=O)R$_{22}$, —SR$_{22}$, —S(O)$_q$R$_{22a}$, —NR$_{22}$R$_{23}$, —NR$_{22}$SO$_2$R$_{23}$, —NR$_{22}$CO$_2$R$_{23}$, —NR$_{22}$C(=O)R$_{23}$, —NR$_{22}$C(=O)NR$_{23}$R$_{33}$, —SO$_2$NR$_{22}$R$_{23}$, —NR$_{22}$SO$_2$NR$_{23}$R$_{33}$, five or six membered heterocyclo or heteroaryl, phenyl, and four to seven membered cycloalkyl, wherein when R$_{20}$ and/or R$_{21}$ independent of each other comprise a cyclic group, each cyclic group in turn is optionally substituted with up to three of $C_{1-4}$alkyl, $C_{1-4}$alkoxy, halogen, hydroxy, haloalkyl, haloalkoxy, amino, alkylamino, and/or cyano;

R$_{22}$, R$_{23}$ and R$_{33}$ are independently selected from hydrogen, alkyl, and substituted alkyl;

R$_{22a}$ is alkyl or substituted alkyl;

R$_{30}$ at each occurrence is selected from hydrogen, alkyl, substituted alkyl, alkenyl, substituted alkenyl, cycloalkyl, and phenyl;

R$_{31}$ and R$_{32}$ at each occurrence are independently selected from hydrogen, alkyl, substituted alkyl, alkenyl, substituted alkenyl, and cycloalkyl;

R$_{32a}$ is alkyl, substituted alkyl, alkenyl, substituted alkenyl, or cycloalkyl;

m is 0, 1 or 2 when ring B is phenyl and 0 or 1 when ring B is pyridyl;

p and q are independently 1 or 2; and
s and t are independently 0, 1 or 2;
which comprises
(a) reacting a cyanostyrene of the structure:

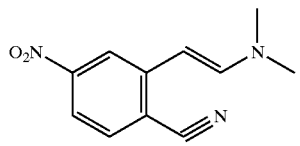

with lithium hexamethyl disilane to form an aminoisoquinoline of the structure:

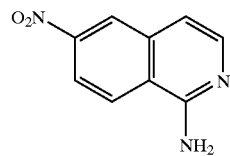

or (b) reacting the cyanostyrene with 2-4-dimethoxylbenzylamine to form an isoquinoline of the structure:

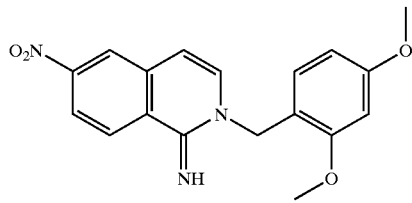

and reacting the isoquinoline with anisole to form the aminoisoquinoline, and employing the aminoisoquinoline to form the compound of formula (I).

Also included within the scope of the invention are novel intermediates utilized in the process.

DETAILED DESCRIPTION OF THE INVENTION

The following are definitions of terms used in this specification. The initial definition provided for a group or term herein applies to that group or term throughout this specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo, alkenyl, alkynyl, nitro, cyano, hydroxy, alkoxy, alkylthio, —$CO_2H$, —C(=O)H, —$CO_2$-alkyl, —C(=O)alkyl, —S(O)$_2$(alkyl), keto (=O), aryl, heteroaryl, heterocyclo, and cycloalkyl, including phenyl, benzyl, phenylethyl, phenyloxy, and phenylthio. The substituents for "substituted alkyl" groups may also be selected from the group consisting of —NR'R", —C(=O)NR'R", —$CO_2$NR'R", —NR'CO$_2$'R", —NR'C(=O)R", —SO$_2$NR'R", and —NR'SO$_2$'R", wherein each of R' and R" is independently selected from hydrogen, alkyl, cycloalkyl, and alkyl substituted with one to two of alkenyl, halogen, haloalkyl, haloalkoxy, cyano, nitro, hydroxy, alkoxy, alkylthio, amino, alkylamino, phenyl, benzyl, phenyloxy, and benzyloxy. Alternatively, R' and R" may together form a heterocyclo or heteroaryl ring. When a substituted alkyl includes an aryl, heterocyclo, cycloalkyl, or heteroaryl substituent, said ringed systems are as defined below and thus may have zero, one, two, or three substituents, also as defined below.

When the term "alkyl" is used in conjunction with another group, e.g., arylalkyl, hydroxyalkyl, etc., the term defines with more specificity a particular substituent that a substituted alkyl will contain. For example, arylalkyl refers to a substituted alkyl group having from 1 to 12 carbon atoms and at least one aryl substituent, and "lower arylalkyl" refers to substituted alkyl groups having 1 to 4 carbon atoms and at least one aryl substituent.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alkenyl groups, respectively, as defined above.

When reference is made to a substituted alkylene, alkenylene, or alkynylene group, these groups are substituted with one to three substitutents as defined above for alkyl groups. A ringed substituent of an alkyl, alkenyl, alkynyl, alkylene, alkenylene, or alkynylene may be joined at a terminal atom or an available intermediate (branch or chain) atom and thus may comprise, for example, the groups:

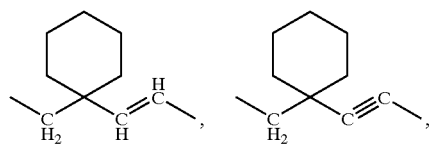

and so forth.

The term "alkoxy" refers to an alkyl group as defined above having one, two or three oxygen atoms (—O—) in the alkyl chain. For example, the term "alkoxy" includes the groups —O—$C_{1-2}$alkyl, —$C_{1-6}$alkylene-O—$C_{1-6}$alkyl, —$C_{1-4}$alkylene-O—$C_{1-4}$alkylene-O—$C_{1-4}$alkyl, O—$C_{1-4}$alkylene-O—$C_{1-4}$alkylene-O—$C_{1-4}$alkyl, and so forth.

The term "alkylthio" refers to an alkyl group as defined above bonded through one or more sulfur (—S—) atoms. For example, the term "alkylthio" includes the groups —S—$C_{1-2}$alkyl, —$S_{1-6}$alkylene-S—$C_{1-6}$alkyl, etc.

The term "alkylamino" refers to an alkyl group as defined above bonded through one or more nitrogen (—NR—)

groups. The term alkylamino refers to straight and branched chain groups and thus, for example, includes the groups —NH($C_{1-12}$alkyl) and —N($C_{1-6}$alkyl)$_2$.

When a subscript is used with reference to an alkoxy, alkylthio or alkylamino, the subscript refers to the number of carbon atoms in the group in addition to heteroatoms. Thus, for example, monovalent $C_{1-2}$alkylamino includes the groups —NH—CH$_3$, —NH—CH$_2$—CH$_3$, and —N—(CH$_3$)$_2$. A lower alkylamino comprises an alkylamino having from one to four carbon atoms.

When reference is made to a substituted alkoxy or alkylthio, the carbon atoms of said groups are substituted with one to three substituents as defined above for alkyl groups. When reference is made to a substituted alkylamino, the carbon and/or nitrogen atoms of these groups are substituted with one to three substitutents appropriately selected from the group of substituents recited above for alkyl groups. Additionally, the alkoxy, alkylthio, or alkylamino groups may be monovalent or bivalent. By "monovalent" it is meant that the group has a valency (i.e., power to combine with another group), of one, and by "bivalent" it is meant that the group has a valency of two. Thus, for example, a monovalent alkoxy includes groups such as —O—$C_{1-12}$alkyl and —$C_{1-6}$alkylene-O—$C_{1-6}$alkyl, whereas a bivalent alkoxy includes groups such as —O—$C_{1-12}$alkylene- and —$C_{1-6}$alkylene-O—$C_{1-6}$alkylene-, etc.

The term "heteroalkyl" is used herein to refer saturated and unsaturated straight or branched chain hydrocarbon groups having 2 to 12 carbon atoms, preferably 2 to 8 carbon atoms, wherein one, two or three carbon atoms in the straight chain are replaced by a heteroatom (O, S or N). Thus, the term "heteroalkyl" includes alkoxy, alkylthio, and alkylamino groups, as defined above, as well as alkyl groups having a combination of heteroatoms selected from O, S, or N. A "heteroalkyl" herein may be monovalent or bivalent, and for example, may comprise the groups —O—(CH$_2$)$_{2-5}$NH—(CH$_2$)$_2$— or —O—(CH$_2$)$_{2-5}$NH—CH$_3$, etc. A "substituted heteroalkyl" has one to three substituents appropriately selected from those recited above for alkyl groups.

The term "acyl" refers to a carbonyl group

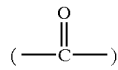

linked to an organic radical including an alkyl, alkenyl, alkynyl, substituted alkyl, substituted alkenyl, or substituted alkynyl group, as defined above.

The term "alkoxycarbonyl" refers to a carboxy or ester group

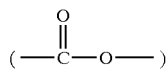

linked to an organic radical including an alkyl, alkenyl, alkynyl, substituted alkyl, substituted alkenyl, or substituted alkynyl group, as defined above.

The term "halo" or "halogen" refers to chloro, bromo, fluoro and iodo.

The term "haloalkyl" means an alkyl having one or more halo substituents, e.g., including trifluoromethyl.

The term "haloalkoxy" means an alkoxy group having one or more halo substituents. For example, "haloalkoxy" includes —OCF$_3$.

The term "sulfonyl" refers to a sulphoxide group (i.e., —S(O)$_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —SO$_2$-alkyl), or bivalent (e.g., —SO$_2$-alkylene, etc.)

The term "sulfonamide" refers to the group —S(O)$_2$NR'R", wherein R' and R" may be hydrogen or alkyl, alkenyl, alkynyl, substituted alkyl, substituted alkenyl, or substituted alkynyl, as defined above. R' and R" may be monovalent or bivalent (e.g., —SO$_2$—NH-alkylene, etc.)

The term "aryl" refers to phenyl, biphenyl, 1-naphthyl and 2-naphthyl, with phenyl being preferred. The term "aryl" includes such rings having zero, one, two or three substituents selected from the group consisting of halo, alkyl, alkenyl, alkynyl, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When an aryl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents, preferably zero or one, selected from the group consisting of halo, alkyl, alkenyl, alkynyl, nitro, cyano, oxo (=O), hydroxy, alkoxy, alkylthio, —CO$_2$H, —C(=O)H, CO$_2$-alkyl, —C(=O)alkyl, keto, =N—OH, =N—O-alkyl, heteroaryl, heterocyclo, a five or six membered ketal (i.e. 1,3-dioxolane or 1,3-dioxane), a four to seven membered carbocyclic ring, —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, a four to seven membered carbocyclic ring, heterocyclo, heteroaryl, —NR'R", —C(=O)NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a cycloalkyl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms, provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halo, alkyl, alkenyl, alkynyl, nitro, cyano, oxo, hydroxy, alkoxy, alkylthio, —CO$_2$H, —C(=O) H, CO$_2$-alkyl, —C(=O)alkyl, keto, =N—OH, =N—O-alkyl, aryl, heteroaryl, cycloalkyl, a five or six membered ketal (i.e. 1,3-dioxolane or 1,3-dioxane), —NR'R", —C(=O)NR'R", —CO$_2$NR'R", —NR'CO$_2$'R", —NR'C (=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O) alkyl, phenyl, benzyl, phenylethyl, phenyloxy, phenylthio, cycloalkyl, heterocyclo, heteroaryl, —NR'R", —C(=O) NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a heterocyclo is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, alkenyl, alkynyl, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, a further monocyclic heteroaryl, —NR'R", —C(=O)NR'R", —CO$_2$NR'R", —NR'CO$_2$'R", —NR'C (=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O) alkyl, phenyl, benzyl, phenylethyl, phenyloxy, phenylthio, cycloalkyl, heterocyclo, heteroaryl, —NR'R", —C(=O) NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a heteroaryl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "carbocyclic" refers to optionally substituted aromatic or non-aromatic 3 to 7 membered monocyclic and 7 to 11 membered bicyclic groups, in which all atoms of the ring or rings are carbon atoms.

When the term "unsaturated" is used herein to refer to a ring or group, the ring or group may be fully unsaturated or partially unsaturated.

The term "metal ion" refers to alkali metal ions such as sodium, potassium or lithium and alkaline earth metal ions such as magnesium and calcium, as well as zinc and aluminum.

Whenever a bond appears in a formula as a dashed-double bond, i.e., with one bond appearing as a dash as in

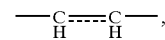

it should be understood that such bonds may be selected from single or double bonds, as appropriate given the selections for adjacent atoms and bonds. For example, in formula I, above, when $X_2$ is N or CH, the bonds linking $R_1$ to $X_2$ and $X_2$ to $C_6$ are single bonds; and when $X_2$ is C, one of the bonds linking $X_2$ to an adjacent atom is a double bond, i.e., either a bond to $R_1$ or to $C_6$ is a double bond.

It should be understood that one skilled in the field may make various substitutions for each of the groups recited in the claims herein, without departing from the spirit or scope of the invention. For example, one skilled in the field may replace a W group recited in the claims with a cyano, halogen, or methyl group. The linker group "L" recited in the claims may be replaced with the group —(R')$_u$—Y'—(R")$_v$— wherein Y' is a Y group recited in formula (I), is a bond, or is selected from —C(=O)—, —[C(=O)]$_2$—, —O—, —NR—, —C(=NR)—, —S(O)$_{1-2}$—, —NRC (=O)NR—, —NRSO$_2$—, or —SO$_2$NR—, wherein R is selected from hydrogen, alkyl, substituted alkyl, alkenyl, substituted alkenyl, a heterocyclo or carbocyclic ring, and so forth, R' and R" may comprise substituted or unsubstituted alkylene, alkenylene, or alkynylene, and u and v may be 0–4. Additionally, the acid group —CO$_2$R$_3$ may be joined to the phenyl or pyridyl ring B with a linker such as a methylene group or replaced with other acid functional groups such as —SO$_3$H, —P(=O)(OR)$_2$, —SO$_2$NHC(=O)R, —C(=O)NHSO$_2$R, —C(=O)NHOH, —[C(=O)]$_2$OR, or tetrazole, wherein R is hydrogen, alkyl, substituted alkyl, cycloalkyl, and so forth.

It should be further understood that for compounds of formula (I), the linker group "L" is inserted into the formula (I) in the same direction set forth in the text. Thus, for example, if L is recited as —CH$_2$—Y—, this means the —CH$_2$— group is attached to Z, and the Y group is attached to the C$_6$ carbon atom i.e., to which X$_2$ is attached, as in:

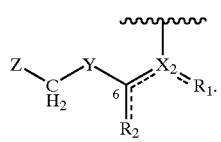

Likewise, when Y is recited as —NR$_{13}$C(=O)—, the carbonyl group C(=O) is attached to the C$_6$ carbon atom and the nitrogen group —NR$_{13}$— is attached to Z, as in many Examples herein. Conversely, when Y is recited as —C(O)NR$_{13}$—, this means the carbonyl group C(=O) is attached to Z and the nitrogen group —NR$_{13}$— is attached to the C$_6$ carbon atom.

Throughout the specification, groups and substituents thereof may be chosen by one skilled in the field to provide stable moieties and compounds.

The compounds of formula (I) form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Various forms of prodrugs are well known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Acamedic Press, 1985);

b) A Textbook of Drug Design and Development, edited by Krosgaard-Larsen and H. Bundgaard, Chapter 5, "Design and Application of Prodrugs," by H. Bundgaard, p. 113–191 (1991); and c) H. Bundgaard, Advanced Drug Delivery Reviews, 8, 1–38 (1992), each of which is incorporated herein by reference.

Compounds containing a carboxy group can form physiologically hydrolyzable esters which serve as prodrugs by being hydrolyzed in the body to yield formula I compounds per se. For example, in compounds of formula (I), prodrugs comprise compounds wherein the upper ring substituent —CO$_2$R$_3$ is a group that will hydrolyze in the body to compounds where said substituent is —CO$_2$H. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include C$_{1-6}$alkylbenzyl, 4-methoxybenzyl, indanyl, phthalyl, methoxymethyl, C$_{1-6}$alkanoyloxy-C$_{1-6}$alkyl, e.g. acetoxymethyl, pivaloyloxymethyl or propionyloxymethyl, C$_{1-6}$alkoxycarbonyloxy-C$_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

The compounds of the instant invention may, for example, be in the free or hydrate form, and may be obtained by methods exemplified by the following descriptions.

METHODS OF PREPARATION

The process of the instant invention is readily carried out as described in Scheme A, wherein $R_a$, $R_b$ and $R_c$ are each independently selected from the group consiting of hydrogen, alkyl, substituted alkyl, alkenyl, substituted alkenyl, alkynyl, substituted alkynyl, heteroalkyl, substituted heteroalkyl, aryl, heteroaryl, heterocyclo, cycloalkyl, halogen, haloalkyl, haloalkoxy, cyano, nitro, —C(=O)NR$_{22}$R$_{23}$, —OR$_{22}$, —CO$_2$R$_{22}$, —C(=O)R$_{22}$, —SR$_{22}$, —S(O)$_q$R$_{22a}$, —NR$_{22}$R$_{23}$, —NR$_{22}$SO$_2$R$_{23}$, —NR$_{22}$CO$_2$R$_{23}$, —NR$_{22}$C(=O)R$_{23}$, —NR$_{22}$C(=O)NR$_{23}$R$_{33}$, —SO$_2$NR$_{22}$R$_{23}$, and —NR$_{22}$SO$_2$NR$_{23}$R$_{33}$, R$_{22}$ and R$_{23}$ are defined as above; and n is 1–3.

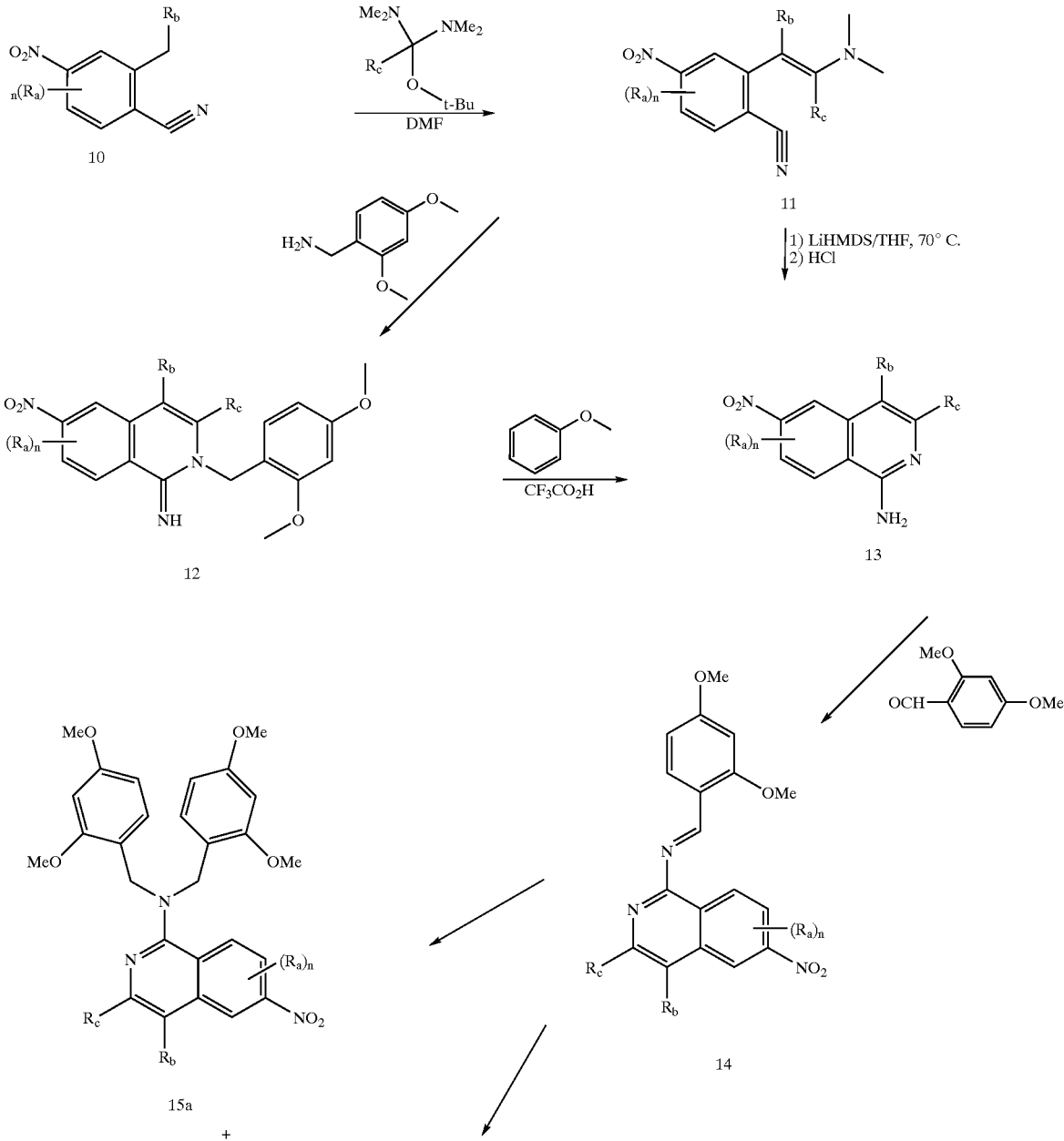

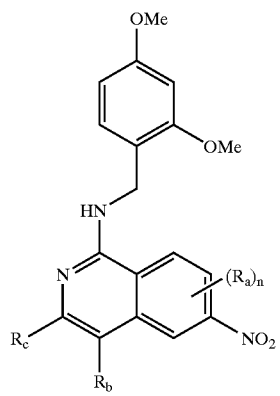

15b

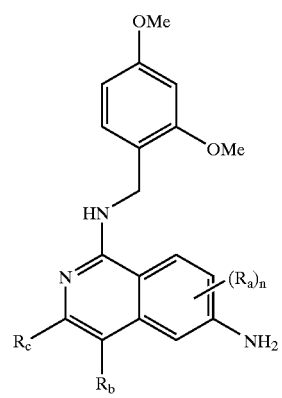

16

Compound 10 was prepared according to *J. Med. Chem.*, 1999, 42, 3510–3519, from 2-methyl-4-nitroaniline. A mixture of compound 10 and 1-(1,1-dimethylethoxy)-N,N,N', N'-tetramethyl-methanediamine in dry DMF (10 mL) was stirred at 70° C. for 2 h under N₂. After cooling to rt, the reaction mixture was treated with hexane, and the solid was collected by filtration and washed with hexane to give compound 11 as black crystals. Compound 11 was converted to compound 13 in two alternate ways.

In one approach, compound 11 was converted to 13 by adding 1N LiHMDS to a solution of 11 in dry THF under N₂. The reaction mixture was stirred at 65° C. for 2 h. After cooling to rt, 12 N HCl was added and the reaction mixture stirred at 50° C. for 1 h. After cooling to rt, the mixture was neutralized with sat'd NaHCO₃, the product extracted with EtOAc, and the organic layer washed with water and sat'd NaCl. The product was concentrated and purified to give compound 13 as a yellow solid.

Alternatively, compound 11 was converted to 13 by first mixing compound 11 and 2,4-dimethoxylbenzylamine in DMF and stirring the mixture at 140° C. for 3 h. The solvent was removed by vacuum distillation and residue treated with EtOAc. The orange solid was collected by filtration and washed with hexane to give compound 12. To a solution of compound 12 in anisole was added TFA. The reaction mixture was stirred at 90° C. for 1 h and the solvent removed under reduced pressure. The residue was treated with sat'd NaHCO₃ (30 mL) and the product collected by filtration and washed with water to afford compound 13.

Compound 13 (366 mg, 1.93 mmol) and 2,4-dimethoxybenzaldehyde were heated for 16 h at 125–130° C. with a stream of nitrogen passing in and out of the reaction flask, and sampling of the reaction mixture at 80° C. indicated conversion to compound 14.

To a solution of 14 and 2,4-dimethoxybenzaldehyde above in THF was added sodium triacetoxyborohydride. The reaction was stirred for 22 h and additional sodium triacetoxyborohydride (1.23g, 5.8 mmol) was added. After 40 h, the reaction was concentrated to an oil which was taken up in EtOAc, water, and dilute sodium bicarbonate. The EtOAc was washed with water (3×), dried (sodium sulfate), and concentrated to an oily residue, which was chromatographed to give 140 mg of compound 15a as a glassy residue and 228 mg of compound 15b as an amorphous solid.

Hydrogenation of compound 15b in EtOAc and MeOH in the presence 10% Pd/C for 1 h at one atmosphere afforded compound 16 as an amorphous solid. Compound 16 was coupled to a substrate and deprotected to produce compounds of formula (I).

We claim:

1. A process for preparing an amino isoquinoline of the structure:

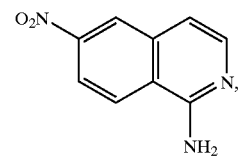

which comprises (a) reacting a cyanostyrene compound of the structure:

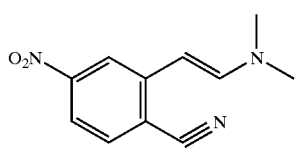

with lithium hexamethyl disilane to form the aminoisoquinoline; or (b) reacting a cyanostyrene of the structure:

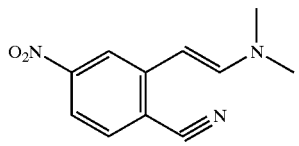

with 2,4-dimethoxylbenzylamine to form an isoquinoline of the structure:

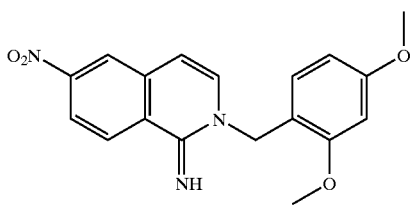

and reacting the isoquinoline with anisole to form the aminoisoquinoline.

2. The process as defined in claim 1 wherein the reaction (a) is carried out under a nitrogen atmosphere.

3. The process as defined in claim 2 including the steps of adding HCl to the starting cyanostyrene compound-lithium hexamethyl disilane reaction mixture and then neutralizing the reaction mixture.

4. A process for preparing a benzylamino isoquinoline compound of the structure:

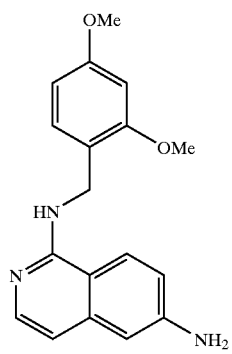

which comprises preparing an aminoisoquinoline

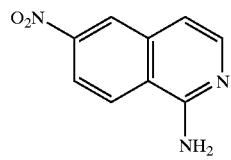

as defined in claim 1 and employing the aminoisoquinoline to prepare the benzylaminoisoquinoline compound.

5. The process as defined in claim 1 where in reaction (b) the isoquinoline is reacted with anisole in the presence of trifluoroacetic acid.

6. A compound having the following structure:

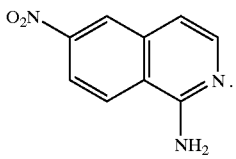

* * * * *